United States Patent [19]

Altadonna

[11] Patent Number: 4,564,521

[45] Date of Patent: Jan. 14, 1986

[54] MEDICATION FOR PAIN RELIEF IN JOINTS OF HUMANS

[76] Inventor: James Altadonna, 90 E. 2nd St., Deer Park, N.Y. 11729

[21] Appl. No.: 591,933

[22] Filed: Mar. 21, 1984

[51] Int. Cl.$^4$ ............................................. A61K 33/18
[52] U.S. Cl. ..................................................... 424/150
[58] Field of Search ......................................... 424/150

[56] References Cited

U.S. PATENT DOCUMENTS

| 54,418 | 2/1890 | Shilton | 424/150 |
| 118,766 | 9/1871 | Whitney | 424/150 |
| 1,867,222 | 7/1932 | Karns | 424/150 |

*Primary Examiner*—Stanley J. Friedman
*Attorney, Agent, or Firm*—Alfred M. Walker

[57] ABSTRACT

A medication for the treatment and relief from pain of the joints of humans is provided said medication consisting of a compound comprised of iodine, sodium iodine, potassium iodine, alcohol and lemon extract.

4 Claims, No Drawings

MEDICATION FOR PAIN RELIEF IN JOINTS OF HUMANS

BACKGROUND OF THE INVENTION

1. Field of Invention

The instant invention relates generally to medication and more specifically said invention relates to a compound for use in the relief of discomfort and pain in the joints of humans.

2. Description of the Prior Art

Heretofore many substances are advertised for use in relieving pain in joints of the human body, said joints being the elbow, knee, thumb area, ankle, neck, wrist, hand and finger, shoulder etc. said substances normally working relatively fast but with the drawback that the effects are not very long lasting.

The aforementioned conditions are most undesirable and it is an object of the instant invention to provide a compound that will provide long lasting results.

SUMMARY OF THE INVENTION

The instant invention provides a compound that with topical applications to the effected area will relieve pain in the various joints of the body.

Accordingly it is an object of this invention to provide a safe means whereby the aforementioned conditions may be treated.

It is a further object of this invention to provide an inexpensive means whereby said conditions may be treated.

To the accomplishment of the above related objects this invention may be embodied in the form illustrated hereinafter it being important to recognize that changes may be made in the specific construction illustrated and described within the scope of the appended claims.

DESCRIPTION OF THE PREFERRED EMBODIMENTS

Turning now descriptively to the actual ingredients of the instant invention, said invention consists of the following:
(a) Iodine
(b) Sodium iodine or potassium iodine
(c) Ethanol alcohol
(d) Lemon extract
(e) Water.

In the preparation of the compound said compound is prepared as follows:

1. Mix the iodine in the proportion of 1 to 5 grams of iodine to 1 liter of completed compound.
2. Combine above ingredients with sodium iodine or potassium iodine in the proportion of 1 to 10 grams of either sodium iodine or potassium iodine to 1 liter of completed compound.
3. Filter the above mixture through carbon filters.
4. Mix with above 400 milliliters of ethanol alcohol.
5. Mix with above 2 milliliters of lemon extract.
6. Add water to above to obtain 1 liter of compound.

It is to be noted that the ethanol alcohol, lemon extract and water are inactive ingredients in the within compound.

Then throughly soak an absorbent material such as a cotton ball and apply topically to the effected area 5 times a day every three hours as follows:

| CONDITION | NUMBER OF DAYS OF TREATMENT |
|---|---|
| Tennis Elbow | 8 Days |
| Knee | 5 Days |
| Thumb Area | 4 Days |
| Ankle | 4 Days |
| Neck | 4 Days |
| Wrist | 4 Days |
| Hand and Finger | 4 Days |
| Shoulder | 4 Days |

With reference to the hands and fingers a tingle may be felt on the second or third day but no concern need be given as this is the normal way said compound operates. In other areas a warm feeling may be felt on the second or third day but this too is normal.

Tennis elbow takes the longest time to heal, that is approximately ten to twelve days. After however five to six days the pain will lessen or may completely disappear but nevertheless the compound should still be applied for an additional two days.

The instant compound effects the joints and works relatively slowly but also relieves the pain for long periods and in some cases the pain may not return for years and if the pain reoccurs reapplication is necessary and when said reapplication is applied the pain is relieved in half of the original time.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

Having regard to the foregoing the following is what I claim as new and inventive:

1. A method of treating pains in joints in humans which comprises the topical application to the skin over an effected joint for absorption by the joint of a solution comprising:
    (a) iodine in the proportion of 1 to 5 grams of iodine to 1 liter of solution;
    (b) sodium iodine in the proportion of 1 to 10 grams of sodium iodine to 1 liter of solution;
    (c) ethanol alcohol in the amount of 400 milliliters
    (d) oil of lemon in the amount of 2 milliliters; and
    (e) water in the amount to obtain 1 liter of solution.

2. A method for making a product, for treating pains in joints in humans by topical application of the product to the skin for absorption by the affected joint, product comprising:
    (a) mixing iodine in the proportion of 1 to 5 grams of iodine and 1 to 10 grams of sodium iodine to 1 liter of completed compound;
    (b) filtering the above mixture through a carbon filter;
    (c) mixing above with 400 milliliters of ethanol alcohol;
    (d) mixing above with 2 milliliters of oil of lemon
    (e) mixing above with water to obtain 1 liter of compound.

3. A method of treating pains in joints in humans which comprises the topical application to the skin over an affected joint for absorption by the joint of a solution comprising:
    (a) iodine in the proportion of 1 to 5 grams of iodine to 1 liter of solution;

(b) potassium iodine in the proportion of 1 to 10 grams of potassium iodine to 1 liter of solution;
(c) ethanol alcohol in the amount of 400 milliliters
(d) oil of lemon in the amount of 2 milliliters; and
(e) water in the amount to obtain 1 liter of solution.

4. A method for making a product for treating pains in joints in humans by topical application of the product to the skin for adsorption by the affected joint comprising:

(a) mixing iodine in the proportion of 1 to 5 grams of iodine and 1 to 10 grams of potassium iodine to 1 liter of completed compound;
(b) filtering the above mixture through a carbon filter;
(c) mixing above with 400 milliliters of ethanol alcohol;
(d) mixing above with 2 milliliters of oil of lemon;
(e) mixing above with water to obtain 1 liter of compound.

* * * * *